United States Patent
Hirose et al.

(10) Patent No.: US 6,339,176 B2
(45) Date of Patent: Jan. 15, 2002

(54) METHOD FOR PRODUCING 4-METHOXYMETHYL-2,3,5,6-TETRAFLUOROBENZENEMETHANOL

(75) Inventors: Taro Hirose; Tatsuya Mori, both of Toyonaka (JP)

(73) Assignee: Sumitomo Chemical Company, Ltd., Osaka (JP)

( * ) Notice: Subject to any disclaimer, the term of this patent is extended or adjusted under 35 U.S.C. 154(b) by 0 days.

(21) Appl. No.: 09/725,472

(22) Filed: Nov. 30, 2000

(30) Foreign Application Priority Data

Dec. 2, 1999 (JP) ............................... 11-343153

(51) Int. Cl.⁷ .............................................. C07C 41/01
(52) U.S. Cl. ........................ 568/628; 568/662; 568/663
(58) Field of Search ................... 568/628, 662, 568/663

(56) References Cited

FOREIGN PATENT DOCUMENTS

| EP | 54360 | | 6/1982 |
|----|-------|---|--------|
| EP | 0 054 360 a2 | | 6/1982 |
| EP | 0 060 617 | * | 9/1982 |
| GB | 2 066 810 | * | 12/1979 |
| GB | 2 097 384 | * | 11/1982 |
| GB | 2 127 013 A | | 4/1984 |

OTHER PUBLICATIONS

Benedict, et al. "Synthesis of Simple . . . Sulfoxide System", Synthesis, vol. 6, 1979, pp. 428–429.

* cited by examiner

*Primary Examiner*—Rosalynd Keys
(74) *Attorney, Agent, or Firm*—Fitch, Even, Tabin & Flannery

(57) ABSTRACT

It provides a production method of 4-methoxymethyl-2,3,5,6-tetrafluorobenzenemethanol to allow 2,3,5,6-tetrafluoro-1,4-benzenedimethanol to react with an inorganic base in water, and then add dimethyl sulfate and a water-immiscible organic solvent selected from the group consisting of hydrocarbons and ethers to the reaction mixture, or to allow 2,3,5,6-tetrafluoro-1,4-benzenedimethanol to react with an inorganic base in water and said water-immiscible organic solvent, and then to add dimethyl sulfate to the reaction mixture.

10 Claims, No Drawings

METHOD FOR PRODUCING 4-METHOXYMETHYL-2,3,5,6-TETRAFLUOROBENZENEMETHANOL

FIELD OF THE INVENTION

The present invention relates to a method for producing 4-methoxymethyl-2,3,5,6-tetrafluorobenzenemethanol by a selective monomethylation of 2,3,5,6-tetrafluoro-1,4-benzenedimethanol.

BACKGROUND OF THE INVENTION

Prior, it has been known that certain ester compounds in which their alcohol part is 4-methoxymethyl-2,3,5,6-tetrafluorobenzenemethanol exhibit an excellent insecticidal effect in EP-54360A. A concrete method for producing 4-methoxymethyl-2,3,5,6-tetrafluorobenzenemethanol is known in the scheme below:

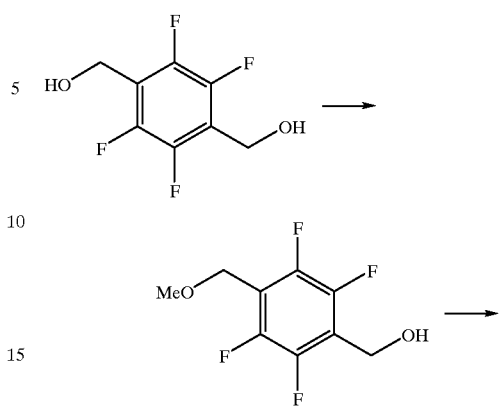

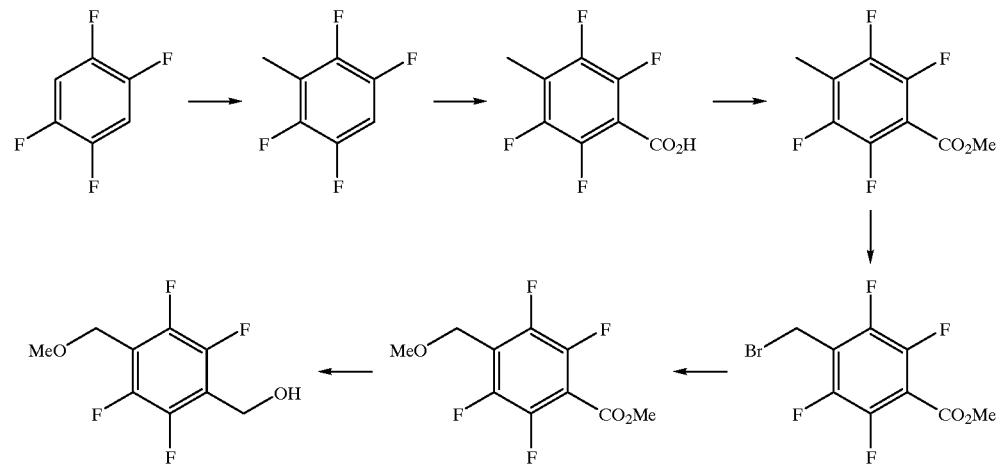

As 1,2,4,5-tetrafluorobenzene is utilized as a starting material and two functional groups of methoxymethyl group and hydroxymethyl group on the benzene ring are constructed separately, the above-mentioned method has many steps. Therefore, the method is not sufficient for economical process in a large scale.

In these situations, a beneficial method for producing 4-methoxymethyl-2,3,5,6-tetrafluorobenzenemethanol is desired to be developed.

SUMMARY OF THE INVENTION

Under these circumstances, 2,3,5,6-tetrafluoro-1,4-benzenedimethanol, which is readily available because it has a symmetric structure and can be easily prepared, was selected as a starting material and the method for producing 4-methoxymethyl-2,3,5,6-tetrafluorobenzenemethanol by a monomethylation was developed.

It is generally difficult to producing a monoalkylated compound in high yield by utilizing a compound having two hydroxy groups which have the same reactivity as a starting material. Because a side reaction of producing a dialkylated compound by further alkylating the monoalkylated compound may be accompanied by a production of the monoalkylated compound.

-continued

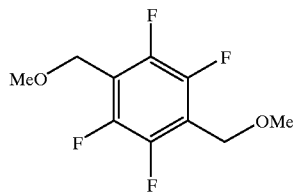

The present inventors have earnestly studied the condition of selective monomethylation of 2,3,5,6-tetrafluoro-1,4-benzenedimethanol, and as a result have found the method for producing 4-methoxymethyl-2,3,5,6-tetrafluorobenzenemethanol in high yield to complete the present invention. The obtained 4-methoxymethyl-2,3,5,6-tetrafluorobenzenemethanol has a relatively high purity and can be simply purified by crystallization out of solution or by distillation in high recovery. Therefore, the method is suitable for the production in an industrial scale.

Namely, the present invention is a method for producing 4-methoxymethyl-2,3,5,6-tetrafluorobenzenemethanol (hereinafter, referred to as the objective compound) which comprises i) allowing 2,3,5,6-tetrafluoro-1,4-benzenedimethanol (hereinafter, referred to as the starting compound) to react with an inorganic base in water, and then ii) adding dimethyl sulfate and a water-immiscible organic solvent selected from the group consisting of hydrocarbons and ethers to the reaction mixture. Another present invention is a method for producing the objective compound which comprises i) allowing 2,3,5,6-tetrafluoro-1,4-benzenedimethanol to react with an inorganic base in water and said water-immiscible organic solvent, and then ii) adding dimethyl sulfate to the reaction mixture.

DETAILED DESCRIPTION OF THE INVENTION

The present method has the following two steps. The first step: Reaction of 2,3,5,6-tetrafluoro-1,4-benzenedimethanol with an inorganic base in water and optionally water-immiscible organic solvent selected from the group consisting of hydrocarbons and ethers. The second step: Obtaining the objective compound by adding dimethyl sulfate and optionally said water-immiscible organic solvent to the reaction mixture. In the second step, the reaction should be carried out in the presence of water and a water-immiscible organic solvent selected from the group consisting of hydrocarbons and ethers. Examples of the water-immiscible organic solvent include aromatic hydrocarbons such as toluene and xylene, aliphatic hydrocarbons such as hexane and heptane and ethers such as t-butyl methyl ether.

The first step is considered a step for preparing salt of the starting compound. It is typically, for example, a preparation of salt of the starting compound by adding the starting compound to an aqueous solution of an inorganic base and mixing them, or by dispersing the starting compound in water, adding an inorganic base to it and mixing them.

Examples of the inorganic base used in the first step include alkali metal hydroxides such as sodium hydroxide and potassium hydroxide. The amount of the inorganic base used in the step is one or more mols, preferably 1 to 2 mols based on 1 mol of the starting compound. The amount of water used as a reaction solvent is one or more parts by weight based on one part of the starting compound, and the amount of water is preferably 3 to 5 parts by weight by reason of good solubility of starting compound salt and of volumetric efficiency.

The reaction temperature is preferably in the range of between 15° C. and 65° C.

One of the preferable conditions is that the mixing in the first step is carried out until most of the used starting compound change to the salt of the starting compound. In that case, the ending point of the first step can be judged at the time for the starting compound to disappear and for the aqueous solution to be clear. The reaction time depends on the reaction temperature and the reaction scale, but is generally 15 minutes to 20 hours.

The solvent used in the first step is water or a mixture of water and the other solvent. When the other solvent is used, the solvent is preferably water-immiscible organic solvent selected from the group consisting of hydrocarbons and ethers. When a hydrocarbon or ether is used in the first step, there is no need to add the hydrocarbon or ether in the second step.

The prepared mixture of the starting compound salt can be utilized for the second step as it is. In other words, the reaction mixture can be utilized for the second step. The salts are exemplified by mono sodium salt or mono potassium salt.

The second step is typically, for example, a preparation of the objective compound by adding dimethyl sulfate and a water-immiscible organic solvent selected from the group consisting of hydrocarbons and ethers to the reaction mixture. When the reaction mixture contains said water-immiscible organic solvent already, the operation of the second step can be an addition of only dimethyl sulfate. The second step may be a reaction of a salt of the starting compound with dimethyl sulfate in water in the presence of said water-immiscible organic solvent.

The amount of dimethyl sulfate utilized in the second step is one or more mols, preferably 1 to 2.5 mols based on 1 mol of the starting compound. It is preferable that the pH value of the aqueous phase is 10 or more, furthermore preferably 13 or more, in which case the second step reaction proceeds well at around room temperature. Though the pH value of the aqueous phase of the reaction mixture may lower depending on the amount of the inorganic base utilized in the first step, an addition of an inorganic base or its aqueous solution can keep the pH value of the water layer in the preferable range that is described above.

The amount of the water-immiscible organic solvent is one or more parts by weight based on one part of the starting compound utilized in the first step. The amount of water used as a reaction solvent is one or more parts by weight based on one part of the starting compound used in the first step, and the water used in the first step is utilized as it is.

The temperature operated in the second step is usually in the range of 0° C. to 100° C., preferably 15° C. to 65° C.

In the second step, it is preferable to perform the reaction essentially in the absence of a quarternary ammonium salt in the reaction system. An addition of the quarternary ammonium salt to the present reaction system increase an amount of a dimethylated by-product of 1,4-di(methoxymethyl)-2,3,5,6-tetrafluorobenzene (hereinafter referred as to the by-product compound). The above-mentioned quarternary ammonium salt means a quarternary ammonium salt utilized in a synthetic reaction generally as a phase transfer catalyst, and is exemplified by tetrabutylammonium bromide, tetrabutylammonium chloride, benzyltrimethylammonium chloride, benzyltriethylammonium chloride and cetyltriethylammonium bromide.

The reaction time of the second step also depends on the reaction temperature and the reaction scale, but is generally 15 minutes to 20 hours.

After the reaction is performed, the reaction mixture is allowed to stand, the layer of the water-immiscible organic solvent is separated and the organic layer is concentrated to give the objective compound. Further, the water layer may be extracted with an organic solvent to recover the objective compound for obtaining high yield. When the extraction is carried out, it is preferable that the pH value of the water layer is 3 or less by reason of extraction efficacy. Examples of the organic solvent utilized for the extraction include aromatic hydrocarbons such as toluene and xylene; aliphatic hydrocarbons such as hexane and heptane; ethers such as t-butyl methyl ether; esters such as ethyl acetate and butyl acetate; and mixtures thereof. The layers of the organic solvent obtained by separation and extraction can be combined and concentrated to give the objective compound.

The objective compound can be purified by usual operations such as crystallization out of a solution, distillation and so on. Especially, crystallization out of solution can give the objective compound having a high purity in high recovery, as the present method gives a relatively high purity of the objective compound.

Examples of the solvent utilized for the crystallization include aromatic hydrocarbons such as toluene and xylene; aliphatic hydrocarbons such as hexane and heptane; ethers such as t-butyl methyl ether and tetrahydrofuran; esters such as ethyl acetate and butyl acetate; alcohols such as methanol, ethanol, propanol, 2-propanol, butanol and t-butyl alcohol; organic acids such as acetic acid, trifluoroacetic acid and formic acid; and water; and mixtures thereof. In the crystallization, the by-product compound, which exists in the crude objective compound in small amount, can be removed almost completely.

The starting compound, 2,3,5,6-tetrafluoro-1,4-benzenedimethanol, can be prepared according to the method described in British Patent publication No. 2,127,013A specification.

EXAMPLE

Hereinafter, the present invention is explained in more detail below referring to production examples and comparative examples but the present invention should not be limited in the following examples.

Production Example 1

Into a reaction vessel that was charged nitrogen, 5.00 g (23.1 mmol) of 2,3,5,6-tetrafluoro-1,4-benzenedimethanol, 15.00 g of water and 1.30 g (23.1 mmol) of potassium hydroxide were charged subsequently, and heated to 60° C. with stirring. At this time, solid 2,3,5,6-tetrafluoro-1,4-benzenedimethanol was completely dissolved to be a clear solution. Then, a mixture of 15.0 g of toluene and 3.07 g (23.1 mmol) of dimethyl sulfate was added at 55±5° C. After stirring at 50±5° C. for 1.5 hours, 0.64 g (11.4 mmol) of potassium hydroxide and 1.51 g (12.6 mmol) of dimethyl sulfate were added. After 1.5 hours, 0.66 g (11.7 mmol) of potassium hydroxide and 1.51 g (12.6 mmol) of dimethyl sulfate were further added and stirred at the same temperature for 1.5 hours. Allowing the reaction mixture to cool to room temperature, the layers of the reaction mixture were separated and the water layer was extracted with 30 ml of ethyl acetate. The organic layers were combined, washed with 30 ml of water, concentrated, and dried under reduced pressure to give 5.22 g of crude 4-methoxymethyl-2,3,5,6-tetrafluorobenzenemethanol. The crude 4-methoxymethyl-2,3,5,6-tetrafluorobenzenemethanol was subjected to content analysis by GC internal standard method (Analytical method 1 given later). GC area percentage of the crude product: 87% of the objective compound, 4% of the starting compound and 8% of the by-product compound Content analysis by GC internal standard method: 85% of the objective compound and 86% of the yield of pure compound

Production Example 2

Into a reaction vessel that was charged nitrogen, 5.00 g (23.1 mmol) of 2,3,5,6-tetrafluoro-1,4-benzenedimethanol, 15.00 g of water and 6.85 g (46.3 mmol) of 27% aqueous sodium hydroxide solution were charged subsequently, and heated to 65° C. with stirring. The starting compound was completely dissolved to be clear solution. Then, the reaction mixture was allowed to cool to room temperature with stirring. At this time, some precipitate was observed. To the reaction mixture, 20.0 g of toluene was added and then 4.33 g (32.6 mmol) of dimethyl sulfate was added dropwise over 7.5 hours at room temperature. After the addition, the pH of the aqueous layer became 13.5. The layers of the reaction mixture were separated, and the pH of the aqueous layer was adjusted to about 3 by adding 10% sulfric acid. The aqueous layer was extracted with 30 ml of ethyl acetate, and the combined organic layers were washed- with 30 ml of water, concentrated, and dried under a reduced pressure to give 5.22 g of crude 4-methoxymethyl-2,3,5,6-tetrafluorobenzenemethanol. The crude 4-methoxymethyl-2,3,5,6-tetrafluorobenzenemethanol was subjected to content analysis by GC internal standard method (Analytical method 1 given later). GC area percentage of the crude product: 85% of the objective compound, 1% of the starting compound and 13% of the by-product compound Content analysis by GC internal standard method: 85% of the objective compound and 86% of the yield of pure compound

Production Example 3

Into a reaction vessel that was charged nitrogen, 10.00 g (47.07 mmol) of 2,3,5,6-tetrafluoro-1,4-benzenedimethanol, 30.00 g of water, 3.77 g (94.13 mmol) of sodium hydroxide and 50.00 g of toluene were charged subsequently. During 20 minutes of stir at room temperature, internal temperature was allowed to go up to 34.0° C., and the starting compound was completely dissolved to be clear solution. To the reaction mixture, 8.75 g (65.8 mmol) of dimethyl sulfate was added in one portion at 30.5° C. Further stirring was continued for 1 h, and the pH of the aqueous layer was adjusted to pH 1.02 by adding 10% sulfric acid for work up. The toluene and aqueous layer were separated and each of them was subjected to content analysis by LC external standard method for the objective compound (Analytical method 2 given later). LC area percentage (corrected) at the final sampling of the reaction course: 87.6% of the objective compound, 4.7% of the starting compound and 6.5% of the by-product compound Content analysis by LC external standard method: total 89.0% of the yield of pure compound

Production Example 4

Into a reaction vessel that was charged nitrogen, 10.00 g (46.26 mmol) of 2,3,5,6-tetrafluoro-1,4-benzenedimethanol, 19.99 g of water and 13.71 g (92.51 mmol) of 27% aqueous sodium hydroxide solution were charged subsequently, and heated to 67.2° C. with stirring. The starting compound was completely dissolved to be clear solution. Then, the reaction mixture was heated to keep the internal temperature 50±3° C. To the reaction mixture, 30.0 g of methyl tert.-butyl ether was added and then 6.14 g (46.26 mmol) of dimethyl sulfate was added in one portion at 50±3° C.

Subsequent portions of dimethyl sulfate were added 2 h(2.5 g), 3.5 h(3.15 g), 5 h(3.1 g), 6.5 h(3.1 g) and 8 h(3.1 g); portions of 27% aqueous sodium hydroxide as well 5 h(6.86 g) and 7 h(6.86 g); later from the first addition of dimethyl sulfate. One hour later from the final addition of dimethyl sulfate, the reaction mixture was cooled down to room temperature. The layers of the reaction mixture were separated. The organic layer was washed with 25 g of 10% aqueous sodium hydroxide for 4 times, concentrated and dried under reduced pressure to give 9.30 g of crude 4-methoxymethyl-2,3,5,6-tetrafluorobenzenemethanol. The crude 4-methoxymethyl-2,3,5,6-tetrafluorobenzenemethanol was subjected to content analysis by GC internal standard method (Analytical method 1 given later). Water layers were all discarded. GC area percentage at the final sampling of the reaction course: 89% of the objective compound, 0% of the starting compound and 10% of the by-product compound Content analysis of organic layer concentrate by GC internal standard method: 83.5% of the objective compound and 75% of the yield of pure compound Reference preparation example (Crystallization purification)

Fifteen grams (15 g) of the crude product of the objective compound (GC area percentage: 89% of the objective compound and 9.5% of the by-product compound) produced by the present method was added to a mixture of 7.5 g of toluene and log of hexane and dissolved completely under heating to 66.3° C. of the inner temperature. The solution was cooled with stirring at a rate of about 20° C. per one hour. At the time of 30° C. of the inner temperature, no crystals were precipitated. After about 10 mg of the purified objective compound was added at 29.9° C. of the inner temperature, the solution was cooled to 20.1° C. of room temperature at the same rate, continued to stir for 2 days, and further cooled with ice. After stirring at 2.5±1° C. of the inner temperature for 3 hours, the solution was filtered at the same temperature. The filtrate was rinsed with 10 g of hexane and dried under a reduced pressure to give 4.05 g of purified 4-methoxymethyl-2,3,5,6-tetrafluorobenzenemethanol. The purified 4-methoxymethyl-2,3,5,6-tetrafluorobenzenemethanol was subjected to content analysis by GC internal standard method (Analytical method 1 given later). GC area percentage: 98.5% of the objective compound and 0.2% of the by-product compound Content analysis by GC internal standard method: 96.6% of the objective compound and 93.3% of the recovery yield of pure compound Comparative Example 1

To a mixture of 0.20 g (5.3 mmol, 64.1% of content) of sodium hydride/oil dispersion and 3.0 g of dimethylformamide, 1.00 g (4.73 mmol) of 2,3,5,6-tetrafluoro-1,4-benzenedimethanol was added at room temperature and stirred for 45 minutes at the same temperature. To the mixture, 0.63 g (4.73 mmol, 95% of content) of dimethyl sulfate was added and stirred for 45 minutes at room temperature. At this time, the starting compound remained in an amount of 28% or more by GC area percentage. To the mixture, 0.05 g (1.3 mmol) of sodium hydride/oil dispersion was added. After the mixture was stirred at room temperature for 1 hour, 0.24 g (1.90 mmol) of dimethyl sulfate was added to the mixture and further stirred for 30 minutes. Two drops of 20% hydrochloric acid was added to the reaction mixture to give a homogeneous solution, 4.98 g of which was subjected to content analysis by GC internal standard method (Analytical method 1 given later). GC area percentage: 41% of the objective compound, 25% of the starting compound and 27% of the by-product compound Content analysis by GC internal standard method: 12% of the objective compound and 24% of the yield of pure compound Comparative Example 2

To a mixture of 1.00 g (4.73 mmol) of 2,3,5,6-tetrafluoro-1,4-benzenedimethanol and 3.0 g of dimethyl sulfoxide, 0.18 g of (4.7 mmol, 64.1% of content) of sodium hydride/oil dispersion was added at room temperature and stirred for 1 hour at the same temperature. To the mixture, 0.60 g (4.73 mmol) of dimethyl sulfate was added and continued to stir for 3 hours. The reaction mixture was poured into 30 ml of 5% hydrochloric acid and extracted with 30 ml of ethyl acetate. The organic layer was washed with water and the solvent was evaporated under a reduced pressure to give 1.11 g of a residue, which was subjected to content analysis by GC internal standard method (Analytical method 1 given later). GC area percentage: 35% of the objective compound, 37% of the starting compound and 16% of the by-product compound Content analysis by GC internal standard method: 26% of the objective compound and 27% of the yield of pure compound Comparative Example 3

At room temperature, 1.00 g (4.73 mol) of 2,3,5,6-tetrafluoro-1,4-benzenedimethanol, 0.65 g (4.73 mmol) of potassium carbonate, 0.75 g (5.94 mmol) of dimethyl sulfate and 3.0 g of acetone were mixed and stirred for 8 hours under heating. The solvent in the reaction mixture was distilled off under a reduce pressure and 30 ml of 5% hydrochloric acid was added to the residue, which was subjected to extract with 30 ml of ethyl acetate. The organic layer was washed with water and the solvent was distilled off under a reduce pressure to give 1.08 g of a residue, which was subjected to content analysis by GC internal standard method (Analytical method 1 given later). GC area percentage: 33% of the objective compound, 51% of the starting compound and 6% of the by-product compound Content analysis by GC internal standard method: 31% of the objective compound and 31% of the yield of pure compound Analytical method 1 (content analysis by GC internal standard method)

Each of gas chromatography device (GC), integrating recorder and auto-injection device was GC14A, C-R5A and AOC-14, which are manufactured by Shimadzu Corporation, respectively used. The column was Capillary Column DB-1 manufactured by J&W Scientific Company (0.53 mm×30m, 1.5 μm of membrane thickness). Concerning GC conditions, the detector was FID, the injection temperature was 250° C., the detector temperature was 250° C. and the column temperature was 80° C. (0 minute), 5° C./minute rising temperature and 300° C. (0 minute, end). The sample solution was injected in an amount of 1 μl.

As an internal standard, 40.0 mg/10.0 ml phenyl benzoate in acetonitrile was prepared and used.

Each standard sample of 43.4 mg, 83.6 mg and 131.0 mg of the objective compound was dissolved in 10.0 ml of the above-mentioned standard solution, respectively. Further, objective sample was dissolved in 10.0 ml of the above-mentioned standard solution and subjected to GC analysis. The peak area ratios of the obtained chromatogram and the internal standard of each sample were calculated to give a calibration curve below, that was utilized for the content analysis. Concentration (mg of the objective compound/10 ml) =60.91007313×area ratio+2.2257 (coefficient of correlation, 1.0000)

Analytical method 2 (content analysis by LC external standard method)

HPLC system was L-7000 series, which is manufactured by Hitachi-Seisakusho Corporeation. The column used is Sumipax ODS A-212 which was manufactured by Sumika-Bunseki Center Corporation. Monitored by UV 270 nm. Eluent used was water—acetonitrile, and graduent condition was that: water: acetonitrile=90:10 (0 min.) to 10:90 (5 min.) for 45 min. Injection volume was 10 μl.

Each standard sample (Assay 99.7% GC area percentage) of 11.4 mg. 34.6 mg, 53.9 mg of the objective compound was dissolved with acetonitrile to make the exact volume of 20.0 ml. The peak areas of the obtained chromatogram of each sample were calculated to give a calibration curve below, that was utilized for the content analysis. Concentration (mg of the objective compound/20 ml)=0.00001094× area+0.1383 (coefficient of correlation, 1.0000)

What is claimed is:

1. A method for producing 4-methoxymethyl-2,3,5,6-tetrafluorobenzenemethanol which comprises i) allowing 2,3,5,6-tetrafluoro-1,4-benzenedimethanol to react with an inorganic base in water, and then ii) adding dimethyl sulfate and a water-immiscible organic solvent selected from the group consisting of hydrocarbons and ethers to the reaction mixture.

2. The method according to claim 1, wherein the inorganic base is an alkali metal hydroxide.

3. The method according to claim 2, wherein the alkali metal hydroxide is sodium hydroxide.

4. The method according to claim 1, wherein the water-immiscible organic solvent is toluene.

5. The method according to claim 1, wherein the water-immiscible organic solvent is t-butyl methyl ether.

6. A method for producing 4-methoxymethyl-2,3,5,6-tetrafluorobenzenemethanol which comprises i) allowing 2,3,5,6-tetrafluoro-1,4-benzenedimethanol to react with an inorganic base in water and a water-immiscible organic solvent selected from the group consisting of hydrocarbons and ethers, and then ii) adding dimethyl sulfate to the reaction mixture.

7. The method according to claim 6, wherein the inorganic base is an alkali metal hydroxide.

8. The method according to claim 7, wherein the alkali metal hydroxide is sodium hydroxide.

9. The method according to claim 6, wherein the water-immiscible organic solvent is toluene.

10. The method according to claim 6, wherein the water-immiscible organic solvent is t-butyl methyl ether.

* * * * *